US009687265B2

United States Patent
Skubitz

(10) Patent No.: US 9,687,265 B2
(45) Date of Patent: Jun. 27, 2017

(54) METHOD AND TOOLS FOR CLEARING THE EPIDURAL SPACE IN PREPARATION FOR MEDICAL LEAD IMPLANTATION

(71) Applicant: Medtronic, Inc., Minneapolis, MN (US)

(72) Inventor: Sean P. Skubitz, Forest Lake, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 675 days.

(21) Appl. No.: 13/752,611

(22) Filed: Jan. 29, 2013

(65) Prior Publication Data
US 2013/0261653 A1 Oct. 3, 2013

Related U.S. Application Data

(60) Provisional application No. 61/618,653, filed on Mar. 30, 2012.

(51) Int. Cl.
| | | |
|---|---|---|
| A61B 17/00 | (2006.01) | |
| A61B 17/3207 | (2006.01) | |
| A61B 17/32 | (2006.01) | |
| A61N 1/05 | (2006.01) | |

(52) U.S. Cl.
CPC .. *A61B 17/3207* (2013.01); *A61B 17/320016* (2013.01); *A61N 1/0551* (2013.01); *A61B 2017/00946* (2013.01); *A61B 2017/320044* (2013.01); *A61B 2017/320056* (2013.01)

(58) Field of Classification Search
CPC ...... A61N 1/0551; A61N 1/0553; A61N 1/05; A61N 1/0558; A61B 17/3401; A61B 17/320016; A61B 17/3421; A61B 2017/3427; A61B 2017/3454; A61B 2017/346; A61B 17/0014; A61B 17/56; A61B 2018/00339; A61B 6018/00964; A61B 2018/0097; A61F 2002/30014; A61F 2002/30018; A61F 2/4675

See application file for complete search history.

(56) References Cited

U.S. PATENT DOCUMENTS

| | | | |
|---|---|---|---|
| 2,487,490 A * | 11/1949 | Sterrett | ................... F16K 31/20 137/426 |
| 5,255,691 A | 10/1993 | Otten | |
| 5,733,322 A | 3/1998 | Starkebaum | |
| 6,308,103 B1 | 10/2001 | Gielen | |

(Continued)

*Primary Examiner* — Gregory Anderson
(74) *Attorney, Agent, or Firm* — Withers & Keys, LLC

(57) ABSTRACT

An epidural space is cleared of fat and scar tissue in preparation for implantation of a medical lead by utilizing a clearing tool. The clearing tool has a flexible body that allows the clearing tool to deflect when entering the epidural space through a window in the vertebral bone and ligaments. The clearing tool is guided into the epidural space and to a target site by a guidewire present in the epidural space. Upon removal of the guidewire and clearing tool, the medical lead is inserted through the window and cleared epidural space until reaching the target site. The clearing tool may include a distal tip with a shape and size that aids in the clearing of the epidural space. The distal tip may be integral to the clearing tool or may be removable so as to allow for different sizes of the distal tip to be installed as needed.

12 Claims, 10 Drawing Sheets

(56) References Cited

U.S. PATENT DOCUMENTS

| | | | |
|---|---|---|---|
| 6,432,104 B1 * | 8/2002 | Durgin | A61B 18/1492 606/39 |
| 6,620,150 B2 * | 9/2003 | Kiemeneij | A61M 25/0041 604/532 |
| 7,022,109 B1 | 4/2006 | Ditto | |
| 7,376,468 B2 | 5/2008 | King et al. | |
| 7,546,164 B2 | 6/2009 | King | |
| 7,695,466 B2 | 4/2010 | Beisel | |
| 7,740,631 B2 | 6/2010 | Bleich et al. | |
| 7,918,849 B2 | 4/2011 | Bleich et al. | |
| 7,922,738 B2 | 4/2011 | Eichmann | |
| 7,963,915 B2 | 6/2011 | Bleich | |
| 2005/0070919 A1 | 3/2005 | Lieberman | |
| 2006/0206118 A1 | 9/2006 | Kim et al. | |
| 2009/0018507 A1 * | 1/2009 | Schmitz | A61B 17/3401 604/164.03 |
| 2010/0331883 A1 | 12/2010 | Schmitz et al. | |
| 2011/0275253 A1 * | 11/2011 | D'Hiver | A61N 1/3752 439/816 |

\* cited by examiner

METHOD AND TOOLS FOR CLEARING THE EPIDURAL SPACE IN PREPARATION FOR MEDICAL LEAD IMPLANTATION

TECHNICAL FIELD

Embodiments relate to the implantation of medical leads used for stimulation within the epidural space. More particularly, embodiments relate to methods and tools for clearing the epidural space in preparation for implantation of a medical lead.

BACKGROUND

Various medical conditions may call for therapeutic electrical stimulation within the epidural space of the spine. Therefore, medical leads capable of delivering stimulation signals are implanted within the epidural space. In some cases, it may be necessary to clear the epidural space as well as the entryway to the epidural space of fatty tissue, scar tissue, and the like in order to provide for easier ingress of the medical lead. This is particularly true for paddle leads that are implanted through a surgical procedure due to the relatively wide distal paddle on the medical lead.

Conventionally, a rigid plastic tool or a soft plastic tool is inserted into the epidural space through a window created within the vertebral bone and associated ligaments. However, the rigid plastic tool presents multiple issues. A first issue is that the rigid plastic provides minimal deflection when entering the epidural space at an angle through the window and thus creates a potential pressure point along the dura of the spinal cord which can cause discomfort and potential paralysis. Another issue is that once in the epidural space, the rigid plastic tool often has less than adequate clearing ability. The soft plastic also presents multiple issues. Once inside the epidural space the soft plastic may deflect in an undesired direction. Additionally, the soft plastic may not have the stiffness to track in the ideal direction. This is particularly true as the width and length of the paddle continues to grow with newer versions of paddle leads where the increased paddle width increases the likelihood of snagging the blockages within the epidural space. Furthermore, the rigid plastic tool with minimal deflection cannot enter at a shallow enough angle to allow for adequate insertion distance needed to reach and clear the target stimulation site.

SUMMARY

Embodiments address issues such as these and others by providing methods for clearing the epidural space and implanting the medical lead and for related tools. Once the window is created, a guidewire is introduced into the epidural space and then a clearing tool is inserted along the path created by the guidewire. The clearing tool can thus be flexible and therefore adequately deflect so that the clearing tool can be inserted an adequate distance to reach the target stimulation site. The tool and guidewire can be removed once the epidural space is cleared, and then the medical lead can be inserted into the cleared epidural space. The tool may include additional features to aid in the clearing of the epidural space, such as a distal tip with a width greater than the body of the tool to aid in the clearing of the space, and in some cases the tip may be removable so as to change the size of the tip to meet the circumstances.

Embodiments provide a method of implanting a medical lead into an epidural space that involves passing a guidewire through a window to the epidural space created within the spinal column. The method further involves passing a tool through the window and into the epidural space by passing the guidewire through a lumen of the tool and cleaning the epidural space by moving the tool further into the epidural space and then retracting the tool. The method additional involves removing guidewire and tool from the epidural space and after removing the guidewire and tool from the epidural space, inserting the medical lead through the window and into a desired position within the epidural space.

Embodiments provide an apparatus for cleaning an epidural space prior to medical lead implantation that includes a flexible elongated body having an inner lumen. The apparatus further includes a guidewire present within the inner lumen and a distal tip present on a distal end of the elongated body, the distal tip having a width greater than a diameter of the elongated body.

Embodiments provide a tool for cleaning an epidural space prior to paddle lead implantation that includes a flexible elongated body having an inner lumen and a distal end with a diameter greater than the lead body. The tool further includes a distal tip present on the distal end of the elongated body, the distal tip having a width greater than the distal end of the elongated body. The distal tip is removable from the elongated body by having two tabs with each tab defining an opening with a diameter greater than the distal end of the elongated body, the tabs having a resting state such that the openings of the tabs are eccentrically aligned to lock the distal tip to the distal end, the distal tip being removable upon pressuring the tabs to force the openings of the tabs to become concentric and pass over the distal end.

Embodiments provide a method cleaning an epidural space prior to paddle lead implantation that involves passing a guidewire through a window to the epidural space created within the spinal column. The method further involves passing a tool through the window and into the epidural space by passing the guidewire through a lumen of the tool and cleaning the epidural space by moving the tool further into the epidural space causing a body of the tool to deflect within the epidural space in proximity to the window and by then retracting the tool. Additionally, the method involves removing the guidewire and the tool from the epidural space, the body of the tool continuing to deflect as the tool is being removed.

DETAILED DESCRIPTION

Embodiments provide methods and tools to clear the epidural space in preparation for implanting a medical lead such as a stimulation lead with a paddle on the distal end. The method involves inserting a guidewire into the epidural space and then using the guidewire to guide a flexible clearing tool into the epidural space and to the target site. Upon removal of the guidewire and tool, the medical lead is then inserted to the target site within the cleared epidural space. The tool may include a distal tip that aids in the clearing process. The distal tip may have a width greater than a body of the tool to further clear the space, and the distal tip may be removable so as to allow for selection of a distal tip with a most appropriate width relative to a given paddle or other width of the medical lead.

Figure 1:
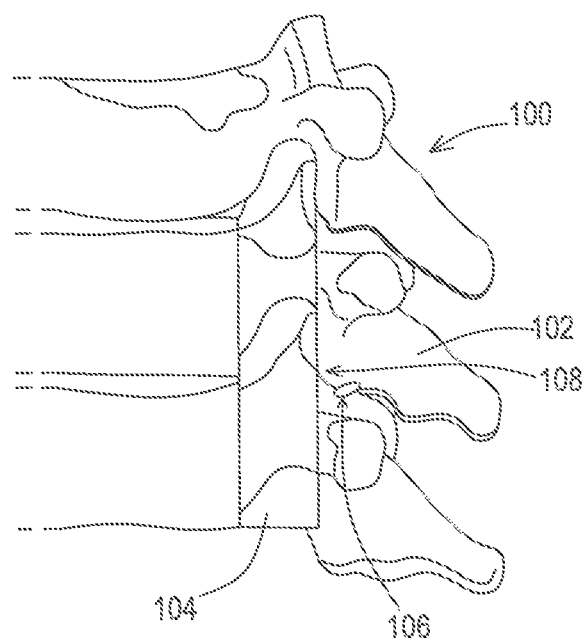
FIG. 1 shows a spine with a window created to access the epidural space.

FIGS. 1-5 illustrate a method of clearing the epidural space and implanting the medical lead within the cleared epidural space. FIG. 1 shows a spinal region 100 of a patient where the implantation of a medical lead is desired. Prior to clearing the epidural space 108, a surgeon has created a window 106 in the spinal region 100 in the conventional manner by cutting through any vertebral bone and ligaments that block entryway to the epidural space 108 that occurs between the dura 104 of the spinal cord and the inner surface of the vertebral bone 102.

Figure 2:
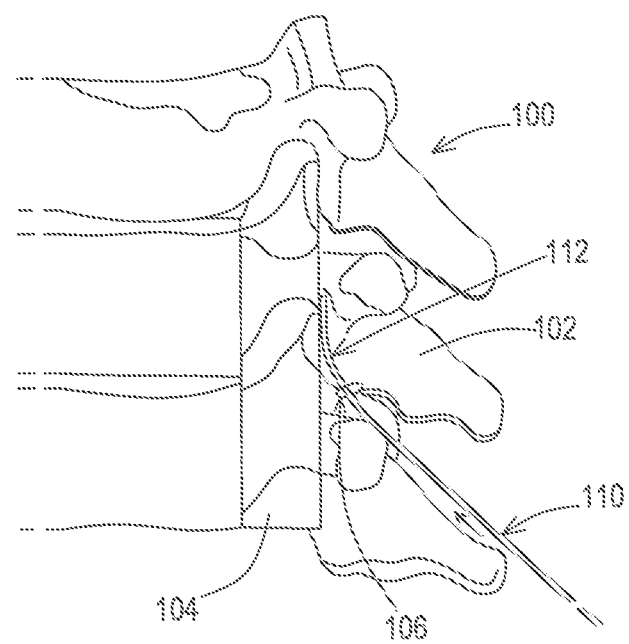
FIG. 2 shows a guidewire being inserted into the epidural space in preparation for insertion of a clearing tool.

FIG. 2 shows the insertion of a guidewire 110 into the epidural space 108 by passing the guidewire 110 through the window 106. As can be seen, the guidewire 110 has deflected to achieve an alignment in the axial dimension of the dura 104. This deflection may be the result of a pre-formed deflection in the area 112 of the guidewire 110 to ensure that the guidewire does not create undue pressure on the dura 104 when entering the epidural space 108. The surgeon continues to feed the guidewire along the axial dimension of the dura 104 until approaching the target site. Alternatively, the guidewire may be inserted but not to the target site, and then may be guided to the target site together with the clearing tool as discussed below. The relatively small diameter of the guidewire 110 allows the guidewire 110 to travel through the window 106 and within the epidural space 108 prior to the window 106 and epidural space 108 having been cleared.

Figure 3:
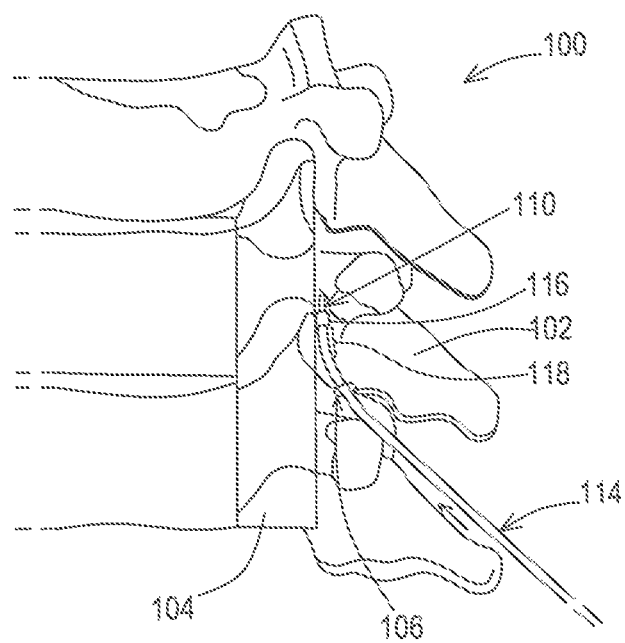
FIG. 3 shows the insertion of the clearing tool that is being guided by the guidewire into the epidural space.

FIG. 3 shows a clearing tool 114 being inserted through the window 106 and into the epidural space 108 by traveling along the guidewire 110. As shown below in FIGS. 6-11, the clearing tool 114 includes a lumen that the guidewire 110 resides within which allows the clearing tool 114 to be guided to the target site within the epidural space 108. The guidewire 110 may have a stiffness greater than that of the larger diameter tool 114 which allows the guidewire 110 to effectively control the path of the tool 114 as the tool 114 is being fed to the target site.

The guidewire 110 may be constructed of various materials to achieve the stiffness to direct the tool 114 while also having the pre-formed deflection near the distal end. One example of guidewire construction is a stainless steel coil.

The body of the tool 114 has a significant amount of flexibility to allow the body of the tool 114 to deflect when entering the epidural space and to allow the tool 114 to extend a significant distance along the axial dimension of the dura 104 while continuing to adequately deflect at the area near the window 106. The body of the tool 114 may be constructed of various materials to provide such flexibility. Examples of such materials include nylon, high density polyethylene, polyurethane, or polypropylene. To aid the clearing process, the body of the tool 114 may also be made radiopaque by including materials such as platinum/iridium, barium sulfate, gold, and/or tungsten so as to be visible during fluoroscopy.

The body of the tool 114 may also include a region 118 that has added stiffness that is small enough to not hinder deflection near the window 106 but aids in the insertion and clearing process by providing axial stiffness without affecting anterior/posterior stiffness. The body of the tool 114 may be relatively soft adjacent to the region 118 and the gradually become stiffer in the proximal direction. For instance, this region 118 may include an inner structure such as a metal braid or a metal coil that allows for some bending yet adds stiffness. Another example is that this region 118 is constructed from a material having a different durometer value from the remaining of the body of the tool 114 to provide the added stiffness.

Figure 4:
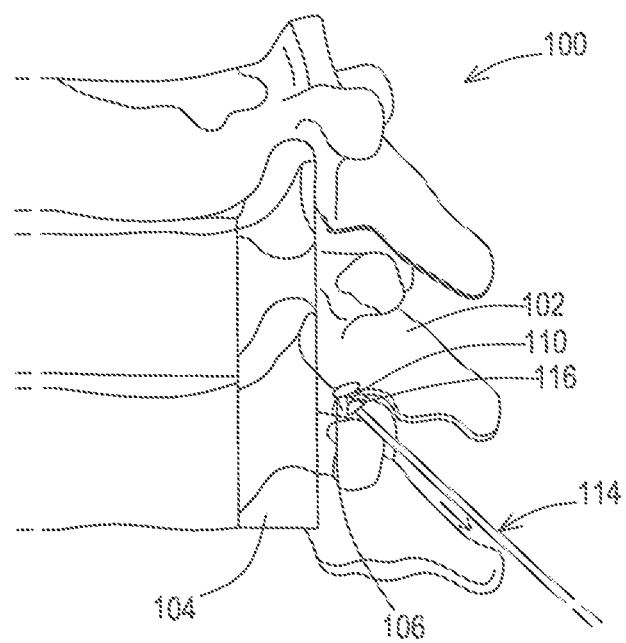
FIG. 4 shows the removal of the clearing tool and guidewire from the epidural space.

The clearing tool 114 is inserted until a distal tip 116 of the clearing tool 114 has reached or exceeded the target site of stimulation within the epidural space 108. At that point, the apparatus including the guidewire 110 and clearing tool 114 may be retracted to further clear the epidural space 108 on the exit route back through the window 106. The retraction of the guidewire 110 and clearing tool 114 is shown in FIG. 4. While the guidewire 110 and clearing tool 114 are being retracted, the body of the clearing tool 114 continues to deflect within the epidural space in proximity to the window 106 to direct the tool 114 out through the window 106 while continuing to avoid undue pressure on the dura 104.

Figure 5:
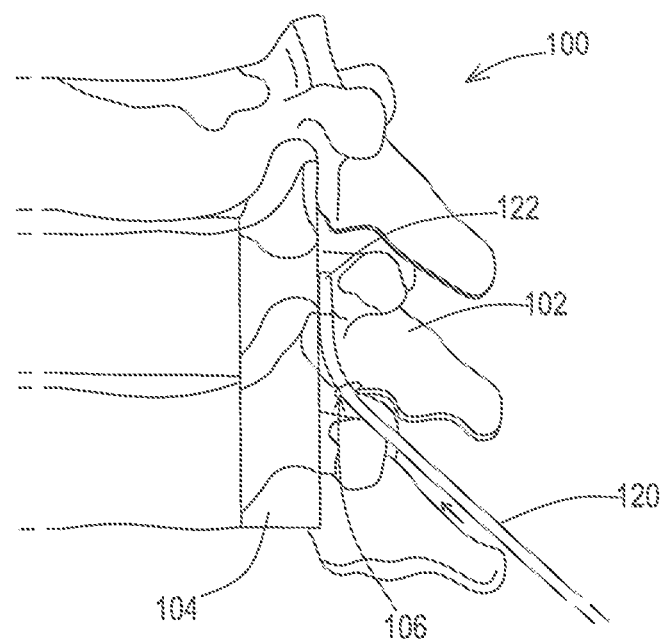
FIG. 5 shows the insertion of a medical lead into the cleared epidural space.

Once the guidewire 110 and clearing tool 114 have been removed from the spinal region 100, the medical lead 120 is then inserted through the window 106 and into the epidural space 108 as shown in FIG. 5. The medical lead 120 continues to be inserted until a distal end 122 which may take various forms such as a paddle of the medical lead 120 reaches the target stimulation site along the axial dimension of the dura 104. Afterward, the medical lead 120 is connected to a medical device that delivers the electrical stimulation signals that are output to through electrodes in the distal end of the medical lead 120. As shown in FIG. 5, the body of the medical lead 120 may exceed that of the clearing tool 114, but the width of the distal tip 116 of the tool 114 has cleared the epidural space 108 so that the additional width of the medical lead 120 and the distal end 122 are not blocked during ingress by obstructions.

Figure 6:
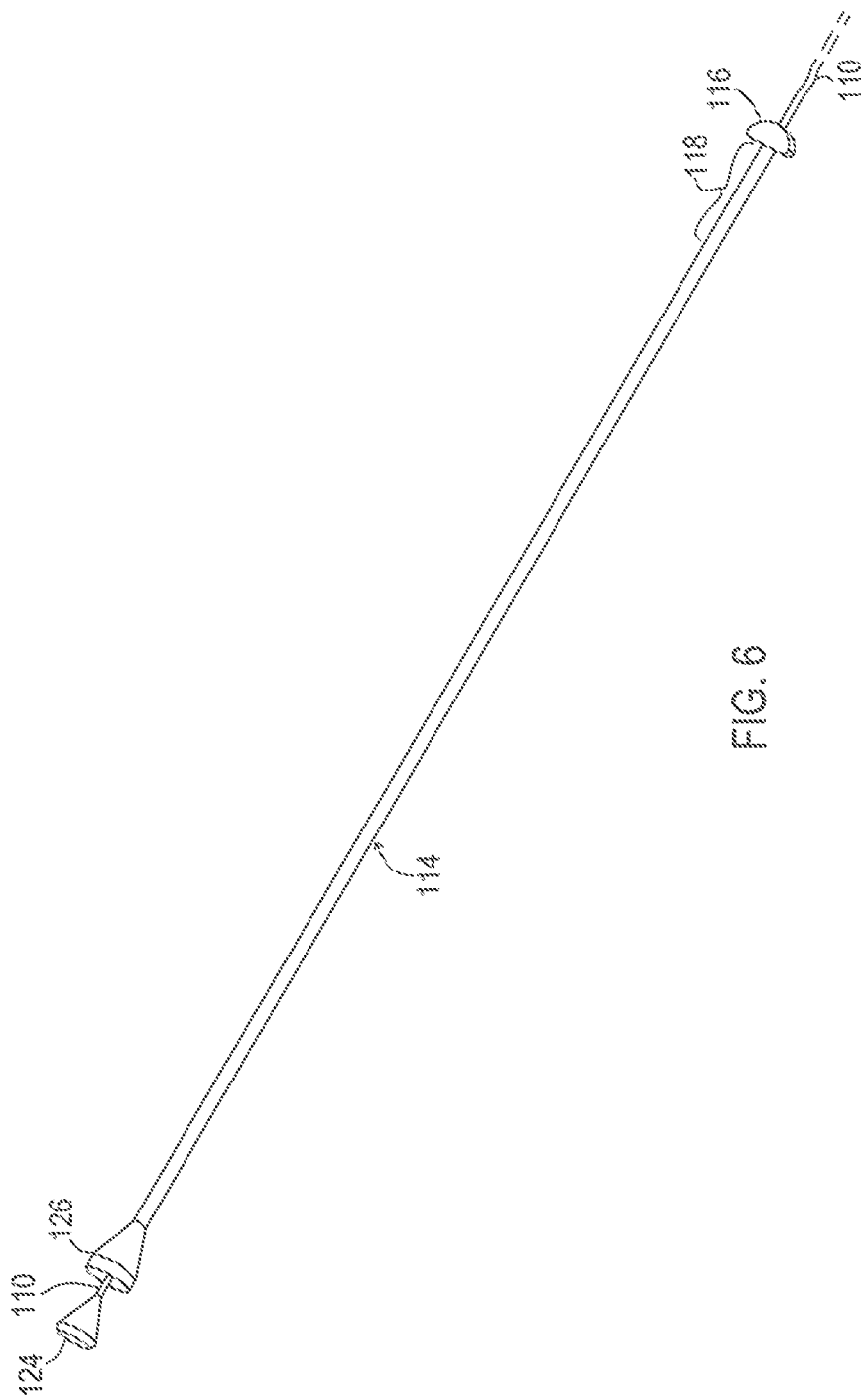
FIG. 6 shows a first example of an apparatus including a guidewire and a clearing tool.

FIG. 6 shows one example of the apparatus including the guidewire 110 and the clearing tool 114. The guidewire 110 includes a proximal hub 124 that a surgeon can manipulate to control and steer the guidewire 110 into position. Likewise, the clearing tool 114 of this example includes a proximal hub 126 that a surgeon can also manipulate to control and steer the clearing tool 114 as it travels along the guidewire 110. In this example, the clearing tool 114 has a distal tip that is integral to the body of the clearing tool 114. Therefore, if a particular width to the distal tip 116 is needed, then a clearing tool 114 having a distal tip 116 of the desired width is selected for the clearing procedure. As shown, this fixed distal tip 116 has a domed shaped, which facilitates clearing of the epidural space. However, it will be appreciated that a variety of shapes are applicable for the distal tip 116.

Figure 7:
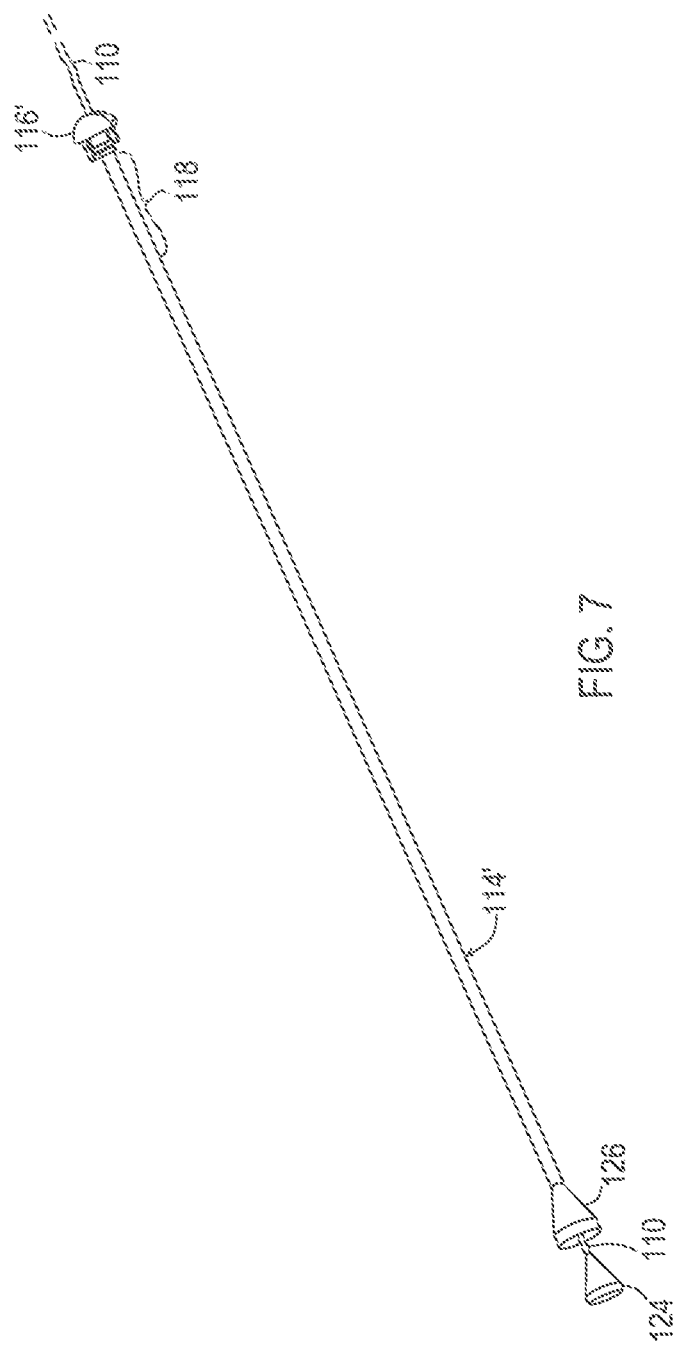
FIG. 7 shows a second example of an apparatus including a guidewire and a clearing tool.

FIG. 7 shows another example of the apparatus including the guidewire 110 and another example of a clearing tool 114'. This clearing tool 114' may include the same flexible body as well as the proximal hub 126. Furthermore, this clearing tool 114' may include a region 118 that has increased stiffness to aid in insertion and clearing. However, the clearing tool 114 has a removable distal tip 116'. The removable distal tip 116' allows the distal tip 116' to be swapped for a most appropriate size for a given medical lead to be implanted. Thus, rather than having to choose an entire clearing tool 114' on the basis of the distal tip size needed, only the distal tip 116' is selected and is installed on the distal end of the clearing toot 114'.

Figure 8:
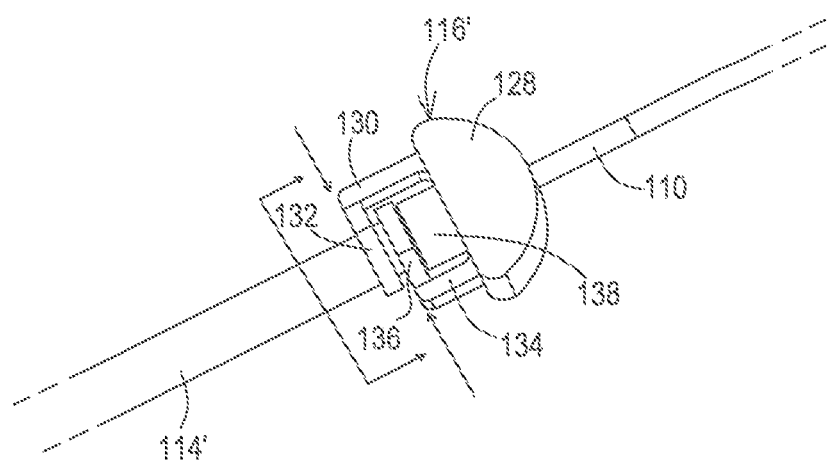
FIG. 8 shows an example of a removable distal tip of a clearing tool of the second example of an apparatus shown in FIG. 7.

FIG. 8 shows an enlarged view of the distal end 138 of the clearing tool 114' as well as the removable distal tip 116' installed on the distal end 138. The distal end 138 of the clearing toot 114' of this example has a larger diameter than the remainder of the body of the clearing tool 114'.

Also in this particular example, the distal tip 116' includes a main body 128 and retention arms 130, 134. Each retention arm 130, 134 terminates at a retention ring 132, 136, respectively. The retention rings 132, 136 retain the distal tip 116' on the distal end 138 by each providing an opening through which the body of the clearing tool 114' passes, with the openings being eccentric. The eccentricity causes the rings 132, 136 to abut the larger diameter distal end 138.

Figure 9:
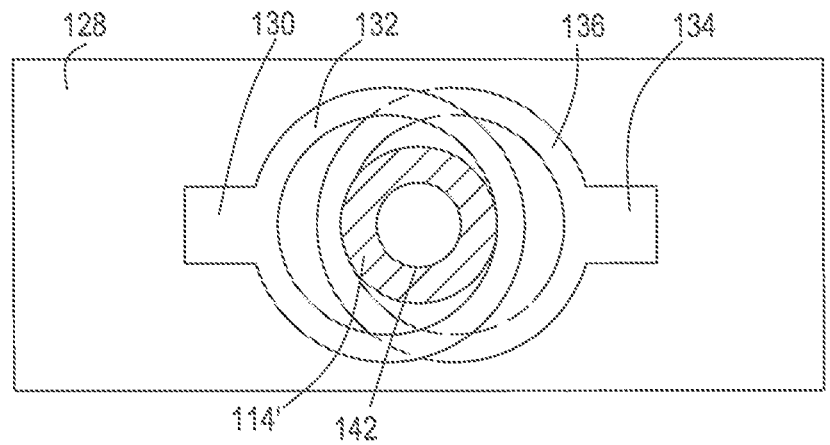
FIG. 9 shows an axial view of the clearing tool with the removable distal tip example from FIG. 8 in a locked position.

This arrangement can be seen in the distal-looking axial view of FIG. 9 which shows the distal tip 116' in the locked position. The arms 130, 134 bias the rings 132, 136 in the outward direction to create the eccentricity of the openings defined by the rings 132, 136. As such, the distal end 138 cannot slide through the opening defined by the eccentric rings 132, 136 that the main body of the clearing tool 114' passes through.

Returning to FIG. 8, then main body 128 may have an aperture that receives a portion of the distal end 138 to further stabilize the distal tip 116' on the distal end 138. In some embodiments, the distal end 116' may have the ability to rotate about the distal end 138. In other embodiments, the distal end 116' may be prevent from rotating either by the degree of friction of the retention rings 132, 136 against the body of the clearing tool 114' and/or by the distal end 138 and an aperture of the main body 128 being keyed to one another.

Figure 10:
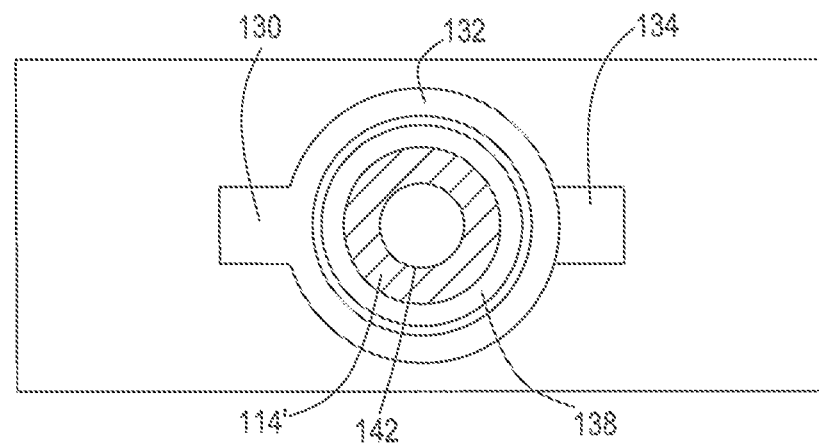
FIG. 10 shows an axial view of the clearing tool with the removable distal tip example from FIG. 8 in a release position.

FIG. 10 shows the configuration that occurs when pressure is being applied inwardly on the retention arms 130, 134. The inward pressure brings the rings 132, 136 into concentric alignment thus creating a larger diameter opening. This concentric alignment allows the distal end 138 to pass through the opening such that the tip 116' is removed. A tip 116' is installed by also providing the inward pressure on the retention arms 130, 134 and sliding the distal end 138 through the resulting opening provided by the concentric rings 132, 136.

Figure 11:
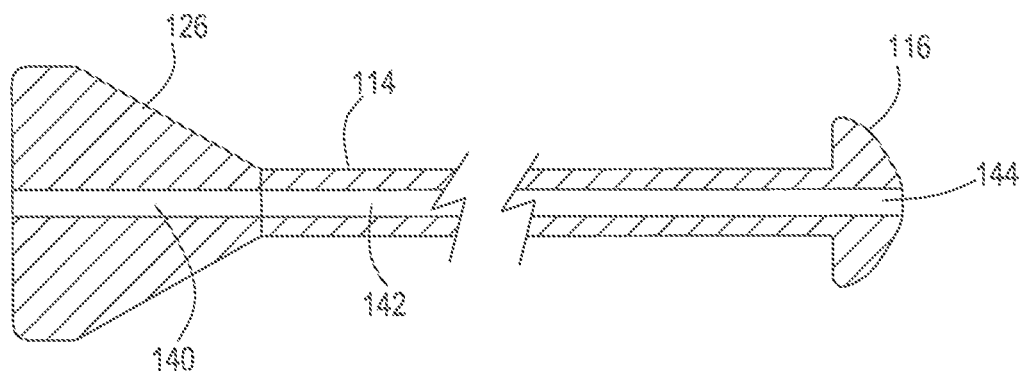
FIG. 11 shows a longitudinal cross-sectional view of an example of the clearing tool.

FIG. 11 shows a longitudinal cross-section to reveal a lumen portion 140 present within the hub 126 as well as a lumen portion 142 present within the body of the clearing tool 114 and a lumen portion 144 present within the integral distal tip 116 of the clearing tool 114 of FIG. 6. These lumen portions 140, 142, 144 create a continuation lumen from end to end and provide a passageway for the guidewire 110 to pass when the clearing tool 114 is being guided into the epidural space 108 by the guide wire 110. The same lumen portions and resulting continuous lumen are present in the clearing tool 114' of FIG. 7 as well.

While embodiments have been particularly shown and described, it will be understood by those skilled in the art that various other changes in the form and details may be made therein without departing from the spirit and scope of the invention.

What is claimed is:

1. An apparatus for cleaning an epidural space prior to paddle lead implantation, comprising:
   a flexible elongated body having an inner lumen;
   a guidewire present within the inner lumen; and
   a distal tip present on a distal end of the elongated body, the distal tip having a width greater than a diameter of the elongated body and having a top leading edge and a bottom leading edge, both the top leading edge and the bottom leading edge each forming an arc laterally relative to an axial dimension of the elongated body and the elongated body further having a top trailing edge and a bottom trailing edge with a planar top surface extending between the top trailing edge and the top leading edge while spanning the full width of the distal tip and with a planar bottom surface extending between the bottom trailing edge and the bottom leading edge while spanning the full width of the distal tip, the top surface and the bottom surface being present on opposite sides of an axial centerline of the elongated body, wherein the distal tip includes a lumen while having the planar top surface and wherein the guidewire is present within the lumen of the distal tip.

2. The apparatus of claim 1, further comprising a hub on a proximal end of the guidewire.

3. The apparatus of claim 1, further comprising a hub on a proximal end of the flexible elongated body.

4. The apparatus of claim 1, wherein the distal tip is integral to the flexible elongated body.

5. The apparatus of claim 1, wherein the distal tip is removable from the flexible body.

6. The apparatus of claim 5, wherein the distal tip includes two tabs with each tab defining an opening with a diameter greater than a diameter of the flexible body.

7. The apparatus of claim 1, wherein a distal region of the flexible elongated body has less flexibility than a more proximal region.

8. A tool for cleaning an epidural space prior to paddle lead implantation, comprising:
   a flexible elongated body having an inner lumen and a distal end;
   a distal tip present on the distal end of the elongated body, the distal tip having a width greater than the distal end of the elongated body, the distal tip being removable from the elongated body by having a tip body that has the width greater than the distal end of the elongated body and having a planar top surface between a leading edge and trailing edge, wherein the distal tip includes a lumen while having the planar top surface and the distal tip having first and second tabs with each tab having a first portion extending proximally from the tip body on opposite sides of the elongated body where the first portion of a first tab and the first portion of the second tab have an overlapping axial position and opposing radial position relative to the elongated body with the elongated body being located directly between the first portion of the first tab and the first portion of the second tab and with each tab having a second portion that extends in a radial direction of the elongated body where the second portion of each tab defines an opening with a diameter greater than a diameter of the distal end of the elongated body, the tabs having a resting state such that the openings of the tabs are eccentrically aligned to lock the distal tip to the distal end, the distal tip being removable upon pressuring the tabs to force the openings of the tabs to become concentric and pass over the distal end.

9. The tool of claim 8, further comprising a hub on a proximal end of the elongated body.

10. The tool of claim 8, wherein a distal region of the flexible elongated body has less flexibility than a more proximal region.

11. The tool of claim 8, wherein the distal tip has an edge forming an arc.

12. The tool of claim 8, wherein the elongated body and the distal tip are constructed of polymers.

* * * * *